(12) United States Patent
Hook et al.

(10) Patent No.: US 10,350,089 B2
(45) Date of Patent: Jul. 16, 2019

(54) DIGITAL TOOL AND METHOD FOR PLANNING KNEE REPLACEMENT

(71) Applicant: Brainlab AG, Munich (DE)

(72) Inventors: Ingmar Hook, Feldkirchen (DE); Christian Brack, Neusaess (DE); Luise Poitzsch, Au i.d. Hallertau (DE); Melanie Stulpe, Munich (DE); Timo Neubauer, Neukeferloh (DE)

(73) Assignee: Brainlab AG, Munich (DE)

( * ) Notice: Subject to any disclaimer, the term of this patent is extended or adjusted under 35 U.S.C. 154(b) by 391 days.

(21) Appl. No.: 14/907,080

(22) PCT Filed: Aug. 14, 2013

(86) PCT No.: PCT/EP2013/067006
§ 371 (c)(1),
(2) Date: Jan. 22, 2016

(87) PCT Pub. No.: WO2015/022022
PCT Pub. Date: Feb. 19, 2015

(65) Prior Publication Data
US 2016/0175055 A1    Jun. 23, 2016

(30) Foreign Application Priority Data
Aug. 13, 2013 (WO) .................. PCT/EP2013/066867

(51) Int. Cl.
*A61F 2/46* (2006.01)
*A61B 34/10* (2016.01)
(Continued)

(52) U.S. Cl.
CPC .......... *A61F 2/4657* (2013.01); *A61B 5/1114* (2013.01); *A61B 5/1127* (2013.01);
(Continued)

(58) Field of Classification Search
CPC .. A61F 2/4657; A61F 5/01; A61F 2002/4668; A61B 90/39; A61B 34/10;
(Continued)

(56) References Cited

U.S. PATENT DOCUMENTS

| 5,936,723 A | 8/1999 | Schmidt et al. |
| 6,384,908 B1 | 5/2002 | Schmidt et al. |

(Continued)

FOREIGN PATENT DOCUMENTS

| DE | 19639615 C2 | 10/1999 |
| DE | 10045376 | 4/2002 |

(Continued)

OTHER PUBLICATIONS

PCT/EP2013/067006 International Search Report dated Apr. 11, 2014.

(Continued)

*Primary Examiner* — Sanjay Cattungal
(74) *Attorney, Agent, or Firm* — Tucker Ellis LLP

(57) ABSTRACT

A medical data processing method of determining a spatial relationship between a marker device (1, 1', 1", 20) and a resection plane (50, 120) associated with an anatomical structure (5, 12) of a patient's body, the marker device (1, 1', 1", 20) being video-detectable by an imaging unit (6), the method being constituted to be executed by a computer and comprising the following steps: a) acquiring imaging unit position data describing a predetermined spatial relationship between the imaging unit (6) and the resection plane; b) acquiring marker device position data describing a spatial relationship between the marker device (1, 1', 1", 20) and the imaging unit (6) based on imaging the marker device (1, 1', 1", 20) with the imaging unit (6) in order to generate an orientation-dependent image appearance of the marker device (1, 1', 1", 20); c) determining, based on the imaging (Continued)

unit position data acquired in step a) and the marker device position data acquired in step b) and based on the orientation-dependent image appearance of the marker device (1, 1', 1", 20), resection plane (50, 120) data describing the spatial relationship between the resection plane (50, 120) and the marker device (1, 1', 1", 20).

19 Claims, 13 Drawing Sheets

(51) Int. Cl.
| | |
|---|---|
| *A61B 34/20* | (2016.01) |
| *A61B 90/00* | (2016.01) |
| *A61B 5/11* | (2006.01) |
| *A61B 5/00* | (2006.01) |
| *A61F 5/01* | (2006.01) |
| *A61B 17/00* | (2006.01) |

(52) U.S. Cl.
CPC ............ *A61B 5/6887* (2013.01); *A61B 34/10* (2016.02); *A61B 34/20* (2016.02); *A61B 90/06* (2016.02); *A61B 90/39* (2016.02); *A61F 5/01* (2013.01); *A61B 2017/00951* (2013.01); *A61B 2034/105* (2016.02); *A61B 2034/2048* (2016.02); *A61B 2034/2055* (2016.02); *A61B 2034/2065* (2016.02); *A61B 2034/2068* (2016.02); *A61B 2090/067* (2016.02); *A61B 2090/363* (2016.02); *A61B 2090/3916* (2016.02); *A61B 2090/3937* (2016.02); *A61B 2090/3983* (2016.02); *A61B 2090/3991* (2016.02); *A61F 2002/4668* (2013.01)

(58) Field of Classification Search
CPC ..... A61B 34/20; A61B 5/6887; A61B 5/1127; A61B 5/1114; A61B 90/06; A61B 2034/2068; A61B 2034/2065; A61B 2017/00951; A61B 2034/2048; A61B 2090/3991; A61B 2090/3983; A61B 2034/105; A61B 2090/363; A61B 2090/3937; A61B 2090/3916; A61B 2090/067; A61B 2034/2055
USPC .................................................. 600/407–480
See application file for complete search history.

(56) References Cited

U.S. PATENT DOCUMENTS

| | | | |
|---|---|---|---|
| 8,059,267 | B2 | 11/2011 | Armstrong |
| 2004/0002642 | A1 | 1/2004 | Dekel et al. |
| 2004/0233461 | A1 | 11/2004 | Armstrong et al. |
| 2005/0234332 | A1* | 10/2005 | Murphy ............... A61B 5/4528 600/426 |
| 2006/0200025 | A1 | 9/2006 | Elliott |
| 2007/0161888 | A1* | 7/2007 | Sherman ............... A61B 17/15 600/409 |
| 2007/0167703 | A1* | 7/2007 | Sherman ............... A61B 5/06 600/407 |
| 2007/0167741 | A1* | 7/2007 | Sherman ............... A61B 90/36 600/424 |
| 2007/0258560 | A1 | 11/2007 | Armstrong et al. |
| 2008/0071195 | A1 | 3/2008 | Cuellar |
| 2010/0100081 | A1 | 4/2010 | Tuma et al. |
| 2011/0286010 | A1 | 11/2011 | Kusik et al. |
| 2013/0218142 | A1 | 8/2013 | Tuma et al. |
| 2015/0057756 | A1* | 2/2015 | Lang ..................... A61B 17/155 623/20.15 |
| 2017/0281297 | A1 | 10/2017 | Tuma et al. |

FOREIGN PATENT DOCUMENTS

| | | | |
|---|---|---|---|
| DE | 10045376 | A1 | 4/2002 |
| EP | 2179703 | B1 | 3/2017 |
| WO | 9938449 | | 8/1999 |
| WO | 0048507 | | 8/2000 |
| WO | 0072047 | A1 | 11/2000 |
| WO | 2006131373 | | 12/2006 |
| WO | 2007051304 | A1 | 5/2007 |
| WO | 2008056180 | A2 | 5/2008 |
| WO | 2009059434 | | 5/2009 |
| WO | 2011012169 | | 2/2011 |
| WO | 2011020505 | | 2/2011 |
| WO | 2011047467 | A1 | 4/2011 |
| WO | 2013052187 | | 4/2013 |
| WO | 2013053398 | | 4/2013 |

OTHER PUBLICATIONS

PCT/EP2013/066867 International Search Report dated Apr. 7, 2014.
European Patent Office, Written Opinion and Search report for PCT/EP2013/066867, dated Apr. 7, 2014, pp. 9.
European Patent Office, Written Opinion and Search report for PCT/EP2013/067006, dated Apr. 4, 2014 pp. 14.

* cited by examiner

DIGITAL TOOL AND METHOD FOR PLANNING KNEE REPLACEMENT

RELATED APPLICATION DATA

This application is a national phase application of International Application No. PCT/EP2013/067006 filed Aug. 14, 2013, published in the English language, which claims priority to International Application No. PCT/EP2013/066867 filed on Aug. 13, 2013, which is hereby incorporated herein by reference.

The invention relates to a method (in particular a data processing method) of determining a spatial relationship between a marker device and a resection plane associated with an anatomical structure of a patient's body. The invention also relates to a corresponding program, a computer executing such a program, a signal wave carrying information representing the program and an apparatus (for example a navigation system) comprising the mentioned computer.

When preparing medical procedures such as a surgical procedure on the knee, it is often required to determine geometric characteristics of the respective leg such as the positions of specific landmarks on the tibia. In known applications, this is achieved by determining the position of the landmark such as the distal end point of the mechanical, in particular proximodistal and/or longitudinal, tibia axis based on for example identifying the malleoli with a tracked pointer device and detecting the position of the pointer device in relation to a bone reference with a stationary camera of a navigation system. This, however, requires the tracked pointer and the bone reference to be visible during landmark acquisition. Moreover, the bone reference needs to be visible whenever the calculated registration is used for navigation purposes. Depending on the conditions in e.g. the operating room, this may not always be the case, especially with the camera being placed several meters away from the operating table.

A specific medical procedure may for example be the creation of a resection plane at the proximal end of the tibia or the distal end of the femur, which needs to have a predetermined orientation relative to the longitudinal axis of the tibia or the longitudinal axis of the femur. Creating this predetermined orientation would be hampered if, for example the acquisition of information about the positions about the required landmarks on the tibia or the femur is hampered.

A problem to be solved by the invention therefore is to provide a method which allows reliable determination of the spatial relationship between a marker device and a resection plane associated with an anatomical structure.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature. A feature of one embodiment which adds an additional function to another embodiment can in particular be added to said other embodiment.

EXEMPLARY SHORT DESCRIPTION OF THE INVENTION

In this section, the invention is described by way of an example. This example shall not be construed to limit the invention to those features which are described in this section. Rather, this section merely offers a concise description of specific features of the present invention.

In order to solve the aforementioned problem, the inventive method is directed to in particular determining a spatial relationship between a marker device and a resection plane which is associated with an anatomical structure such as a tibia or a femur. The marker device preferably is video-detectable and comprises a graphical feature which can be detected by an imaging unit and can be analysed from an image thus generated. The imaging unit preferably is a camera of a handheld data processing device such as a mobile phone or a personal digital assistant. Preferably, the imaging unit is placed in a predetermined spatial relationship relative to the resection plane, so that in particular the position and orientation of the imaging unit relative to the resection plane is known. Preferably, the marker device rests in a global coordinate system while being imaged by the imaging unit. Based on imaging the marker device with the imaging unit (which has the predetermined spatial relationship relative to the resection plane), an orientation-dependent image appearance of the marker device is generated which serves as a basis for determining for the spatial relationship between the resection plane and the marker device. On this basis, the spatial relationship between the resection plane and the marker device can be determined, for example in order to determine whether the resection plane has the envisaged position and orientation with regard to the anatomical structure (i.e. the tibia or the femur). In one embodiment of the invention, the marker device has a fixed position relative to the anatomical structure, in another embodiment of the present invention, the marker device does not have a fixed position relative to the anatomical structure, in particular the anatomical structure can be moved relative to the marker device while imaging the marker device with the imaging unit. During this movement, the imaging unit preferably has a fixed spatial relationship relative to the anatomical structure.

GENERAL DESCRIPTION OF THE INVENTION

In this section, a description of the general features of the invention is offered. In particular, the preferred features of the invention are described in detail.

The inventive method is in particular a data processing method, further particularly a medical data processing method and a data processing method usable in connection with medical applications. The method is preferably constituted to be executed by a computer and comprises the following preferred steps and features.

Preferably, the inventive method is suitable for determining a spatial relationship (in particular at least one of position and orientation) between a marker device and a resection plane, in particular it is suitable to determine at least one of position and orientation of the marker device relative to the resection plane and/or to determine at least one of position and orientation of the resection plane relative to the marker device. The resection plane is preferably associated with an anatomical structure of a patient's body. The anatomical structure may be any anatomical structure, i.e. it may be an anatomical structure comprising both hard and soft tissue. Preferably, however, the anatomical structure comprises hard tissue and is in particular a bony structure. According to two preferred embodiments, the anatomical structure is a tibia or a femur. The resection plane is associated with the anatomical structure in the sense that it is envisaged that the resection plane shall be generated in the anatomical structure. However, it is neither an explicit nor an implicit feature which is required to implement the disclosed invention that the resection plane has already been generated when the inventive method is carried out. In particular, the inventive method does not involve or encompass an invasive step which would represent a substantial physical interference to the body requiring professional medical expertise to be carried out and entailing a substantial health risk even when carried out with the required professional care and expertise. In particular, no part of the inventive method involves or encompasses a surgical step, and in particular the inventive method does not involve or encompass a step of treating a human or animal body using surgery or therapy. Rather, the invention is directed to in particular data processing. For at least this reason, no surgical or therapeutic activity (in particular no surgical or therapeutic step) is necessitated or implied by carrying out the invention.

The marker device preferably is video-detectable for detection by an imaging unit. The imaging unit preferably is an imaging unit operating in the visible wavelength spectrum, in particular the imaging unit is a camera, more particularly a digital camera, advantageously the digital camera of a handheld mobile device such as a mobile phone or a personal digital assistant. Preferably, the imaging unit is a video camera which is combined with a display unit in a single device. The display unit is in particular a monitor (in particular an LCD monitor) of the mobile device to which the video camera belongs. The display unit and the imaging unit are preferably disposed in a common housing. The marker device being video-detectable means in particular that the marker device is visible in the visible wavelength spectrum so that it can be detected (in particular imaged) by an imaging unit operating in that wavelength range. Advantageously, the marker device is two-dimensional and allows determining its distance and orientation from and to, respectively, the imaging unit based on analysing its image appearance in an image taken by the imaging unit. For example, the marker device is a planar marker device comprising a plurality of graphical markers, in particular graphical patterns (also called graphical marker patterns). These patterns preferably have a predetermined geometry which is in particular known to the inventive method such that, on the basis of analysing (in particular segmenting) an image of the marker device taken by the imaging unit allows to determine the spatial relationship between the marker device and the imaging unit can be determined.

Preferably, image unit position data is acquired which describes a predetermined spatial relationship between the imaging unit and the resection plane. In particular, this predetermined spatial relationship has been established beforehand. The predetermined spatial relationship is at least one of position and orientation of the imaging unit relative to the resection plane. For example, the imaging unit is fastened to a medical device or the anatomical structure at a position which has a known spatial relationship relative to the position of the resection plane. As an example, the imaging unit is fastened to a medical device which is a cutting block for cutting the proximal end of the tibia or the distal end of the femur, respectively, which has been fastened to the anatomical structure. The cutting block comprises a slot for insertion of a cutting device (e.g. a saw). The position and orientation of the slot define the position and orientation of the resection plane. It is notable that it is not necessary to perform any surgical activity in order to fasten the cutting block. Rather, it would suffice to position the cutting block with a known spatial relationship relative to the envisaged resection plane, which may happen for example before the patient is placed ready for operation. Such may be done for example for the framework of pre-operative planning.

Preferably, marker device position data is acquired which describes a spatial relationship between the marker device and the imaging unit. This is done preferably based on (in particular by) imaging the marker device with the imaging unit in order to generate an orientation-dependent image appearance of the marker device. The marker device preferably has a predetermined position which is advantageously fixed and further advantageously represents a fixed spatial relationship relative to the resection plane. This is particularly suitable for determining the longitudinal axis of the tibia. For determining the centre of rotation of a hip joint, the marker device preferably does not have a fixed spatial relationship relative to the resection plane and may be placed away from the anatomical structure, for example on a structure having a fixed spatial relationship in a global coordinate system, for example the marker device may be fastened to an operation table. The predetermined spatial relationship between the imaging unit and the resection plane is preferably established such that the marker device is in the viewing area of the imaging unit in order to enable acquisition of the marker device position data. The spatial relationship between the marker device and the imaging unit is at least one of the position and the orientation of the marker device relative to the imaging unit or vice versa (namely of the imaging unit relative to the marker device). The image appearance of the marker device in an image of the marker device acquired by the imaging unit depends on the spatial relationship, in particular on at least one of the orientation and the position, between the imaging unit and the marker device. One of the objects of the present invention is to determine the orientation of the resection plane, for example in a varus/valgus direction and the anteroposterior direction of the tibia. Another object of the invention is to determine a centre of rotation of the hip joint which is characterized in particular by the range of angles which the femur is able to go through during rotation in the hip joint. In this context, it suffices in particular to have knowledge of the orientation of the marker device relative to the unit (in particular relative to the imaging plane of the imaging unit, which may be defined by the planar extension of an imaging chip used in a digital imaging unit) in order to determine data describing the angles which characterise the orientation of the resection plane relative to the characteristic geometry of the anatomical structure with which it is associated.

The spatial relationship between the resection plane and the marker device, in particular the orientation of the resection plane relative to the marker device and/or the orientation of the marker device relative to the resection plane, is described in particular by resection plane data which is determined preferably based on the imaging unit position data and the marker device position data as well as based on the orientation-dependent image of the marker device. In particular, information about the video-detectable geometry of the marker device is predetermined and known to the inventive method. Analysis of the image of the marker device taken by the imaging unit (for example by a known image segmentation algorithm) may serve to determine the orientation of the marker device relative to the imaging unit on the basis of that image. Thereby, the angular relationship between the resection plane and the marker device can be determined, since the spatial relationship between the imaging unit and the resection plane is predetermined. For example, the predetermined spatial relationship is established by establishing a mechanical contact between contact of a surface of an adapter and the cutting block, wherein the adapter is fastened to the imaging unit in a fixed and known (in particular predetermined) spatial relationship and wherein the surface is for example planar and is inserted into the slot of a cutting block which defines the resection plane. The cutting block preferably has a predetermined spatial relationship relative to the anatomical structure and is in particular attached to the anatomical structure so as to define the position of and orientation of the resection plane relative to the anatomical structure.

The spatial relationship between the resection plane and the marker device may additionally to the orientation also describe the position of the resection plane relative to the marker device (and/or the position of the marker device relative to the resection plane). Based on information about this position, resection height data describing a resection height associated with the resection plane is preferably determined. The resection height describes the distance from the marker device (and/or the tip of a pointer having a known spatial relationship relative to the marker device) to the resection plane. For example, the resection height describes the longitudinal extension (i.e. the thickness) of the bone part which is to be resected from the proximal end of the tibia or the distal end of the femur, respectively. In particular, the marker device is placed with a predetermined (in particular known) spatial relationship (in particular position) relative to an anatomical land mark such as the ankle of the leg on the body side of the leg with which the resection plane is associated. The positions of two landmarks can be determined for example by identifying the left and right malleoli of the respective tibia and fibula. The spatial relationship between the ankle and for example the natural proximal end of the tibia can be determined from for example medical image data of the tibia which was acquired beforehand for example by x-ray or computer tomography imaging. For example, a marker device is placed (with a predetermined (in particular known) spatial relationship in the cutting slot of a cutting block placed in a predetermined position relative to the tibia (such that the position and orientation of the cutting slot defines the desired position and orientation of the resection place on the tibia), and a pointer to which the imaging unit is fastened in a predetermined (in particular known) and preferably fixed spatial relationship is placed on a point on the proximal surface of the tibia while the imaging unit detects the marker device. From the resulting image, the distance between the position of the marker device (and therefore the cutting slot which represents the resection plane) and the marker device and/or the pointer tip can be determined. This distance equals the resection height.

According to a preferred embodiment, the anatomical structure is a tibia and the resection height data (in particular the value of the resection height) is determined by identifying the position of a point on the proximal surface of the tibia with a pointer tool while imaging it with the imaging unit. In that case, the pointer tool is preferably provided with a video-detectable marker device such as the one described above. According to another preferred embodiment, the anatomical structure is a femur and the resection height data is determined by identifying the position of a point on the distal surface of the femur. In particular, of the pointer tool has a predetermined and in particular known spatial relationship relative to the imaging unit. For example, the pointer tool is attached to the imaging unit.

According to a preferred embodiment of the invention, the marker device is placed on the patient's ankle on the body side with which the body plane is associated, for example in case the tibia is a right tibia, the marker device is placed on the patient's right ankle. Preferably, the marker device is provided with a fastening mechanism such as a clip mechanism or a strap mechanism which allows placing the marker device in a predetermined spatial relationship relative to the landmarks such as the malleoli. Detection of the marker device by the imaging unit and correspondingly determining its position then allows determining the position of the landmarks. For example, a pointer tool fixedly fastened to the imaging unit is placed in a known spatial relationship relative to a resection plane at the proximal tibia end while the imaging unit images the marker device placed on the ankle.

Preferably, the resection plane data is determined as soon as the marker device is in the viewing area of the imaging unit. In particular, a computer which is operatively coupled to the imaging unit and executes an image analysis algorithm for analysing images taken by the imaging unit is provided with predetermined information about the possible appearance of the marker device and on this basis continuously checks whether the marker device is being imaged or not. If it is detected that the marker device is being imaged, the computer executes the steps required to determine the resection plane data.

Preferably, the anatomical structure is a tibia and resection plane angular data is determined which describes at least one of a varus/valgus angle and a flexion angle of the resection plane relative to in particular the longitudinal axis and the anteroposterior axis of the tibia. The resection plane angular data is determined based preferably on the resection plane data (in particular on the orientation of the resection plane relative to the marker device) and further based on the following:

data describing the position of the proximal end point of the proximodistal tibia axis (i.e. the longitudinal tibia axis);

data describing the position of the distal end point of the mechanical, in particular proximodistal and/or longitudinal, tibia axis;

data describing the orientation of the anteroposterior axis at the proximal end of the tibia on the body side with which the resection plane is associated (in particular on the corresponding body side).

The above-mentioned three types of data describing positions of specific points (or axes) on the tibia may be determined for example from medical image data in particular relative to the position of an easily identifiable landmarks such as the malleoli. Alternatively, the data describing the position of the proximal end-point of the proximodistal axis of the tibia is acquired by identifying the position of the proximal end point of the proximodistal axis of the tibia with a pointer tool, wherein the spatial relationship between the pointer tool and the imaging unit is preferably predetermined, in particular known to the inventive method. For example, the imaging unit is attached to a pointer tool which is provided with a planar abutment piece which is designed to be flush with a resection plane when placed onto the resection plane. In particular, the spatial relationship between the planar abutment piece and the imaging unit is predetermined, in particular known, and preferably such that it is possible to place the planar abutment piece on the resection plane while imaging the marker device with the imaging unit.

According to another preferred embodiment, the anatomical structure is a femur and resection plane angular data is determined which describes at least one of a varus/valgus angle and a flexion angle of the resection plane relative to in particular the longitudinal (i.e. proximodistal) femur axis and the anteroposterior plane of the femur. In this case, the resection plane angular data is determined based on the resection plane position data, in particular based on the orientation of the resection plane relative to the marker device, and based on the following:

data describing the position of the centre of rotation of the femoral head on the body side with which the resection plane is associated (i.e. on the femur of the corresponding body side);

data describing the position of the distal end point of the mechanical, in particular proximodistal and/or longitudinal, femur axis;

data describing the orientation of the anteroposterior axis at the distal end of the femur on the body side with which the resection plane is associated.

In this embodiment, the marker device is preferably based in a fixed position which is not located on the patient's body, for example it is positioned at a fixed position in a global coordinate system which serves to determine positional information in the framework of the inventive method. For example, the marker device is attached to the operating table. A predetermined and fixed spatial relationship between the imaging unit and the femur is established, for example by inserting an adapter to which the imaging unit is attached into a cutting block having a predetermined and fixed spatial relationship relative to the femur (in particular relative to the position of the resection plane on the femur), and the femur is brought into at least preferably four different positions while imaging the marker device with the imaging unit in order to determine the spatial relationship between the position of the femur relative to the marker device in each of these at least four positions. On this basis, a rotational profile of the femur is acquired and the centre of rotation of the femoral head in the hip joint is determined. The data describing the position of the distal end point of the mechanical, in particular proximodistal and/or longitudinal, femur axis and the data describing the orientation of the anteroposterior axis of the femur is acquired preferably from medical image information. Alternatively, the data describing the position of the distal end point of the mechanical, in particular proximodistal and/or longitudinal, femur axis is acquired by identifying the distal end point of the mechanical, in particular proximodistal and/or longitudinal, femur axis with the pointer tool, for example the aforementioned planar abutment piece fastened to the imaging unit, while imaging the marker device with the imaging unit.

The invention also relates to an apparatus comprising the aforementioned imaging unit for imaging the marker device, a display unit for displaying an image of a marker device acquired with the imaging unit, and a computer which is configured to execute a program which, when running on the computer, causes a computer to perform the method steps as described above. The imaging unit and the display unit are operatively connected to the computer.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Definitions

In the following, definitions of specific terminology are disclosed which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). A computer herein is a technical computer which comprises in particular technical, in particular tangible components, in particular mechanical and/or electronic components. Any device mentioned herein is a technical, in particular tangible device.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

The method in accordance with the invention is in particular a data processing method. The data processing method is preferably performed using technical means, in particular a computer. The data processing method is preferably constituted to be executed by or on a computer, in particular it is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows to display information outputted by the computer e.g. to a user. An example of a display device is an augmented reality device (also called augmented reality glasses) which may be used as goggles for navigating. A specific example of such augmented reality glasses is Google Glass (trademark of Google Inc.). An augmented reality device may be used to both input information into the computer by user interaction and to display information outputted by that computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

DESCRIPTION OF THE FIGURES

In the following, the invention is described with reference to the Figures, wherein the invention shall not be limited only to the features described with reference to and shown in the Figures.

FIG. 1 illustrates a video-detectable marker device 1 comprising a plurality of graphical marker patterns 2 which are for example planar and have a geometry which is predetermined and preferably known to the disclosed method. The marker device 1 is attached to a patient's ankle 4 with an attaching mechanism 3 embodied by a strap. The marker device is constituted to fit with a predetermined spatial relationship onto the malleoli of the ankle 4.

FIG. 2 shows a video-detectable marker device 1' having graphical marker patterns 2 on its surface. The graphical marker patterns 2 are for example planar and have a geometry which is predetermined and preferably known to the disclosed method. The marker device 1' is inserted into the cutting slot 91 of a cutting block 9. The marker device 1' may also be removed from the cutting slot 91 again as indicated by the double arrow by FIG. 2. The marker device 1' is inserted into the cutting slot 91 that it is oriented in the anteroposterior (ap) direction of the anatomical structure (e.g. the tibia or the fibula) with which the envisaged resection plane is associated. In particular, the position and orientation of the cutting slot 91 relative to the anatomical structure determines the position and orientation of the resection plane relative to and/or on the anatomical structure. The cutting slot 91 is therefore preferably oriented in that anteroposterior direction. The cutting block 9 is in particular suitable to be used for a resection procedure on at least one of the proximal end of the tibia and the distal end of the femur.

FIG. 3 shows the set-up of FIG. 2 with an additional video-detectable marker device 1" which is basically constituted in the same manner as marker device 1'. The marker device 1" is attached to for example a part of the cutting block 9 which does not move relative to the bone to be resected (i.e. relative to the tibia or the femur), for example a cutting block base 92 (i.e. a base part of the cutting block 9), whereas the marker device 1' and the cutting slot 91 in which it is inserted may move relative to the position of the marker device 1". In particular, the cutting slot 91 can be moved relative to the cutting block base 92 along the mechanical axis of the respective bone in order to allow positioning of the cutting slot and therefore the resection plane on the respective bone at the desired position. Detection of the marker device 1' and preferably (simultaneously) also the marker device 1" can therefore be used to determine the resection height on the respective end of the bone. Furthermore, the detected position of the marker device 1" is used as a basis for determining the centre of rotation of the femur if the cutting block has a predetermined (in particular known) and preferably fixed position relative to the femur.

FIG. 4 shows a planar adapter 7 having a planar abutment piece 71 which can be placed on a finished resection plane. In order to support correct positioning of the planar abutment piece 71 on the resection plane, the planar abutment piece 71 comprises a placement aid 72 embodied by a central hole in the planar abutment piece 71 and a printing on the visible side of the planar abutment 71 which indicates the anterior and posterior directions of the bone. The planar abutment piece 71 can be used to determine the angular orientation of the resection plane and to determine whether the resection plane is flat. In particular, the planar abutment piece 71 is designed to fit flush on a resection plane and embodies in particular an ideally planar surface on the side which is to be placed on the resection surface, i.e. on its side lying on the other side of the drawing plane of FIG. 4. To this end, the adapter 7 may be brought into a predetermined and preferably fixed spatial relationship (in particular at least one of position and orientation) relative to the imaging unit 6. For example and as shown in FIG. 5, both the adapter 7 and the imaging unit 6 may be fastened to a handle 80 so that they have a predetermined (i.e. in particular known) and preferably fixed spatial relationship relative to one another.

FIG. 6 shows the set-up of FIG. 5 in which the planar adapter 7 has been replaced by a pointer adapter 8 which also has a predetermined and preferably fixed spatial relationship relative to the imaging unit 6. Both the imaging unit 6 and the pointer adapter 8 are fastened in a preferably fixed spatial relationship to the handle 80. The pointer adapter 8 allows to identify positions in space by pointing the tip of the pointer adapter 8 at the respective position, in particular placing the tip on that position. The imaging unit 6 may then for example detect a marker device lying in its field of view (also called viewing area 62) and for example determine the spatial relationship between the position identified by the tip of the pointer device 8 relative to the marker device.

FIG. 7 shows a graphical output of a display unit 61 which is operatively coupled to a computer to which also the imaging unit 6 is operatively coupled. The computer processes the image data generated by the imaging unit 6 and on the basis of image analysis determines positional information and for example resection plane angular data (indicated by the varus and slope angles shown in FIG. 7) and the resection height data (indicated by the 9.0 mm resection value shown in FIG. 7). The corresponding information is then output on the display unit 61 as shown in FIGS. 5 and 6, the imaging unit 6 and the display unit 61 as well as the computer conducting the data processing can be combined in a single housing and can be embodied by for example a handheld data processing device such as a smartphone or a personal digital assistant comprising a digital camera as the imaging unit 6.

FIGS. 8 and 9 show an embodiment of the disclosed method for verifying a resection plane 50 associated with a tibia 5. FIG. 8 shows the set-up used for planning the resection plane 50, in particular for positioning the cutting block 9 on the tibia such that the position and orientation of the resection plane 50 defined by the position and orientation of the cutting slot 91 is as desired. According to FIG. 8, a marker device 1 is attached to the patient's ankle 4 and the cutting block 9 comprising the cutting slot 91 is positioned on the proximal end of the tibia 5 while a video-detectable marker device 1' is placed in the cutting slot 91. The resection height on the proximal end of the tibia 5 (comprising the proximal end point 55 of the mechanical tibia axis 53, cf. FIG. 15) is determined by identifying the proximal end point 55 of the tibia 5 with the pointer adapter 8 attached to the handle 80 to which also the imaging unit 6 is attached. Both markers 1 and 1' are in the viewing area 62 of the imaging unit 6. Since the position of the marker device 1 defines the position of the distal end point 54 of the tibia 5, the distance between the position of the marker device 1 and the position of the marker device 1' can be determined by analysis of an image taken of both the marker device 1 and the marker device 1' at the same time by the imaging unit 6. Due to the known spatial relationship between the tip of the pointer adapter 8 and the imaging unit 6, the tibia resection height 52 (cf. FIG. 11a) can be determined as the distance between the position of the tip of the pointer adapter 8 and the position of the tibia resection plane 50 defined by the position of the marker device 1' when it is placed in the cutting slot 91. Since the marker device 1' and preferably also the marker device 1 are oriented in the anteroposterior direction of the tibia 5, it is also possible to check whether the orientation of the tibia resection plane 50 is as desired. Preferably, the tibia resection plane 50 is parallel to the planar surface of the marker device 1 to which graphical marker patterns 2 are applied.

FIG. 9 shows the set-up for verifying the position and orientation of the finished tibia resection plane 50 after the proximal end portion of the tibia 50 corresponding to the resection height 52 has been removed. The planar adapter 7 is attached to the handle 80 to which also the imaging unit 6 is attached. The planar abutment piece 71 has a predetermined (in particular known) and preferably fixed spatial relationship relative to the imaging unit 6 and is placed flush on the tibia resection plane 50. The marker device 1' is preferably removed from the cutting slot 91 and the marker device 1 is in the viewing area 62 of the imaging unit 6 when the planar abutment piece 71 is placed on the tibia resection plane 50. The placement aid 72 is placed under visual control on the tibia resection plane 50 such that it has a predetermined position relative to the proximal end point 125 of the tibia axis 53, in particular the proximal end point 125 remains visible through the hole embodying the placement aid 72 when the planar abutment piece 71 is properly positioned. By analysing the image of the marker device 1 taken by the imaging unit 6 while holding the planar abutment part 71 on the tibia resection plane 50, it is thus possible to determine the position and orientation of the tibia resection plane 50. Additionally, it is possible to determine whether the tibia resection plane 50 is planar as shown in FIG. 11b by for example visually and tactilely checking whether the planar abutment piece 71 (which is considered to be ideally planar) properly fits on the tibia resection plane 50.

FIGS. 12a to 12c show a first embodiment of a method for verifying the position and orientation of a resection plane 120 associated with a femur 12. FIG. 12a shows the set-up for planning the position and orientation of the femur resection plane 120. A video-detectable marker device 1" is attached to the cutting block base 92 which preferably has a fixed spatial relationship relative to the femur 12. The cutting slot 91 is movable relative to the cutting block base 92 so that its position and orientation can be adjusted as desired in accordance with the desired position and orientation of the femur resection plane 120. A video-detectable marker device 20 comprising graphical marker patterns 2 is placed at a fixed position in a global coordinate system, for example it is attached to the operating table on which the patient is placed. In particular, the marker device 20 does not have a fixed spatial relationship relative to the femur 12. The graphical marker patterns 2 are for example planar and have a geometry which is predetermined and preferably known to the disclosed method. The imaging unit 6 is attached to the handle 80 and held so that both the marker device 20 and the marker device 1" are in the viewing area 62 of the imaging unit 6. The femur 12 is then rotated into for example four different positions in order to determine the centre of rotation of the femur 12. The centre of rotation coincides with at least one of the distal and proximal end points 124, 125 of the femur axis (123), in particular it coincides with the distal end point 124 of the femur axis 123, and serves in particular as a base position from which the position of the femur resection plane 120 is determined.

FIG. 12b shows the set-up for determining the femur resection height 122 (cf. FIG. 10a). The femur resection height 122 is determined by placing the tip of the pointer adapter 8 on the distal end point 124 of the femur axis 123 to identify the position of the distal end point 124, while imaging the marker device 1' (which is placed in the cutting slot 91) to determine the position of the marker device 1'. The femur resection height 122 is determined as the distance between the positions of the tip of the pointer adapter 8 and the position of the marker device 1'. The orientation of the cutting slot 91 and therefore the orientation of the envisaged femur resection plane 120 is determined by determining the orientation of the marker device 1' by imaging it and comparing it to the position of the centre of rotation of the femur 12 and the distal end point 124 of the femur axis 123 which is identified by the tip of the pointer adapter 8. Compared to the set-up of FIG. 12a, it is no longer necessary to have the marker device 20 in the viewing area 62 of the imaging unit 6. In addition to the set-up of FIG. 12a, a marker device 1' is placed in the cutting slot 91 so that the position and orientation of femur resection plane 120 can be determined relative to the position and orientation of the marker device 1" which is still attached to the cutting block base 92. The pointer adapter 8 is placed on the distal end of the femur 12 and is attached to the handle 80 to which also the imaging unit 6 is attached. Both markers 1' and 1" are in the viewing area 62 of the imaging unit 6 so that they can be simultaneously imaged. Based on analysis of a thus-obtained image of both marker devices 1' and 1", the position and orientation of the femur resection plane 120 which is defined by the position and orientation of the marker device 1' when it is placed in the cutting slot 91 can be determined. In particular, the orientation of the marker device 1" is suitable as a reference for determining a proper orientation of the femur resection plane 120 based on the information about the position of the centre of rotation determined as described with regard to FIG. 12a. The femur resection height 122 is illustrated in FIG. 10a and is determined based on the information about the predetermined and fixed spatial relationship between the tip of the pointer adapter 8 and the imaging unit and the position of the marker device 1'.

FIG. 12c shows the set-up for determining the position and orientation of the finished femur resection plane 120 after a portion of the distal end of the femur 12 corresponding to the femur resection height 122 has been removed from the femur 12. The marker device 1' is removed from the cutting slot 91, while the marker device 1" remains attached to the cutting block base 92. The planar adapter 7 comprising the planar abutment piece 71 is attached to the handle 80 to which also the imaging unit 6 is attached. The planar abutment piece 71 is placed on the femur resection plane 120. Based on predetermined (in particular known) information about the predetermined (in particular known) and preferably fixed spatial relationship between the planar abutment piece and the imaging unit 6, the position and orientation of the femur resection plane 120 relative to the position and orientation of the marker device 1" can be determined by imaging the marker device 1" with the imaging unit 6 when placing the planar abutment piece 71 on the femur resection plane 120. Additionally, it is possible to visually and tactilely determine whether the femur resection plane 120 is planar as desired and shown in FIG. 10b.

FIGS. 13a to 13c illustrate a second embodiment of the method for determining the position and orientation of the femur resection plane 120. FIG. 13a shows the set-up for planning the position and orientation of the femur resection plane 120. In this set-up, the marker device 1' is based in the cutting block 91 and no further marker device is attached to the cutting block 9. The additional (external) marker device 20 is placed as described in relation to FIG. 12a. Both marker devices 1' and 20 are in the viewing area 62 of the imaging unit 6 which is attached to the handle 80, and the femur is moved into for example four different positions while imaging both marker devices 1' and 20 with the imaging unit 6. This allows to determine the centre of rotation of the femur 12. The position of the marker device 1' relative to the centre of rotation is determined. On that basis, also the position of the cutting slot 91 and thus the femur resection plane 120 can be determined relative to the centre of rotation of the femur 12. The position of the centre of rotation is defined in particular relative to the position of the marker device 20 which is used in all steps of the embodiment according to FIGS. 13a to 13c.

In FIG. 13b, the femur resection height 122 (cf. FIG. 10a) and the orientation of the femur resection plane 120 are determined by placing the tip of the pointer adapter 8 on the distal end of the femur 12 while imaging both marker devices 1' and 20. The pointer adapter 8 is attached to the handle 80 to which also the imaging unit 6 is attached. The spatial relationship between the tip of the pointer adapter 8 and the imaging unit is predetermined (in particular known) and preferably fixed. Since the spatial relationship between the centre of rotation of the femur 12 and the marker device 20 is known, image analysis of an image of both the marker device 1' and the marker 20 allows to determine whether the femur resection plane 120 defined by the orientation of the marker device 1' is as desired. The position of the cutting slot 91 and/or the marker device 1' which defines the position of the femur resection plane 120 and thus the resection height 122 is determined by analysing the image of the marker device 1' and determining the distance between the position of the femur resection plane 120 (defined by the position of the marker device 1') and the position of the tip of the pointer adapter 8 as shown in FIG. 10a.

FIG. 13c shows the step of then determining the position and orientation of the finished femur resection plane 120. The marker device 1' is removed from the cutting slot 91 while the marker device 20 remains in a previous position. The planar adapter 7 comprising the planar abutment piece 71 is attached to the handle 80 to which also the imaging unit 6 is attached. As before, the spatial relationship between the planar abutment piece 71 and the imaging unit 6 is predetermined (in particular known) and preferably fixed. The planar abutment piece 71 is placed on the finished femur resection plane 120 while imaging the marker device 20 with the imaging unit 6. Since the spatial relationship between the centre of rotation of the femur 12 and the marker device 20 is known from the steps described above with regard to FIG. 13a, it is thus possible to determine the position and orientation of the femur resection plane 120 relative to the centre of rotation of the femur 12 by analysing the image of the marker device 20 taken with the imaging unit 6 while the planar abutment piece 71 is held on the femur resection plane 120. Additionally, it is possible to determine whether the femur resection plane 120 is planar as desired and shown in FIG. 10b.

FIGS. 14a to 14c show a third embodiment for determining the position and orientation of the femur resection plane 120. FIG. 14a shows the set-up for planning the position and orientation of the femur resection plane 120. The imaging unit 6 is provided with an adapter 63. The imaging unit 6 and the adapter 63 have a predetermined (in particular known) and preferably fixed spatial relationship relative to one another. The adapter 63 is placed in the cutting slot 91. The imaging unit 6 then images the external marker device 20 which is placed at a fixed position in a global coordinate system, for example the marker device 20 is fixed to the operating table on which the patient is placed. While imaging the marker device 20 with the imaging unit 6, the femur 12 is rotated in for example four different positions in order to determine its centre of rotation and the spatial relationship between the centre of rotation and the marker device 20. Based on the known spatial relationship between the imaging unit 6 and the cutting slot 91 (which defines the position and orientation of the femur resection plane 120), one can determine whether the position and orientation of the femur resection plane 120 (which is defined by in particular its spatial relationship relative to centre of rotation of the femur 12 and/or relative to the position and orientation of the marker device 20) is as desired.

FIG. 14b illustrates the set-up for determining the femur resection height 122 (cf. FIG. 10a) and the distal end point 124 of the femur axis 123 which is conducted as explained above with regard to FIG. 13b.

FIG. 14c illustrates the set-up for determining the position and orientation of the finished femur resection plane 120 which corresponds to the set-up explained above with regard to FIG. 13c.

FIG. 15 shows the anatomy of a lower extremity comprising a femur 12, a tibia 5 and a fibula 51. The mechanical axis of the femur (the femur axis) is indicated by a semidashed line and the reference sign 123. The femoral rotation centre corresponding to the proximal end point 125 of the femur axis 123 and the distal end point 124 of the femur axis 123 are also illustrated. Furthermore, the proximal end point 55 of the tibia axis 53 and the distal end point 54 of the tibia axis 53 are shown. The distal end point 54 of the tibia axis 53 corresponds to approximately the centre between the medial and lateral malleolus.

Figure 1:
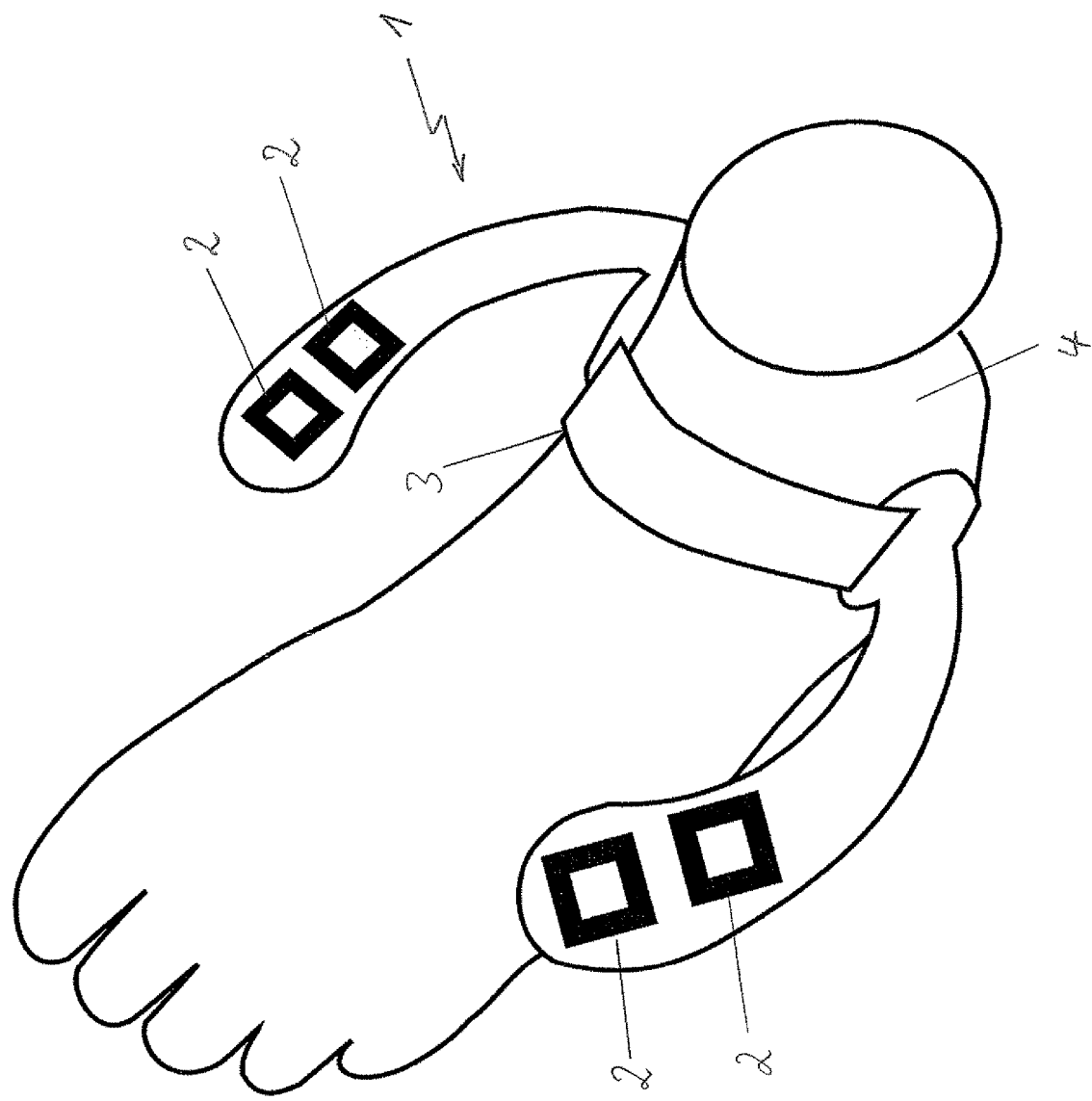
FIG. 1 shows a marker device attached to a patient's ankle.
Figure 2:
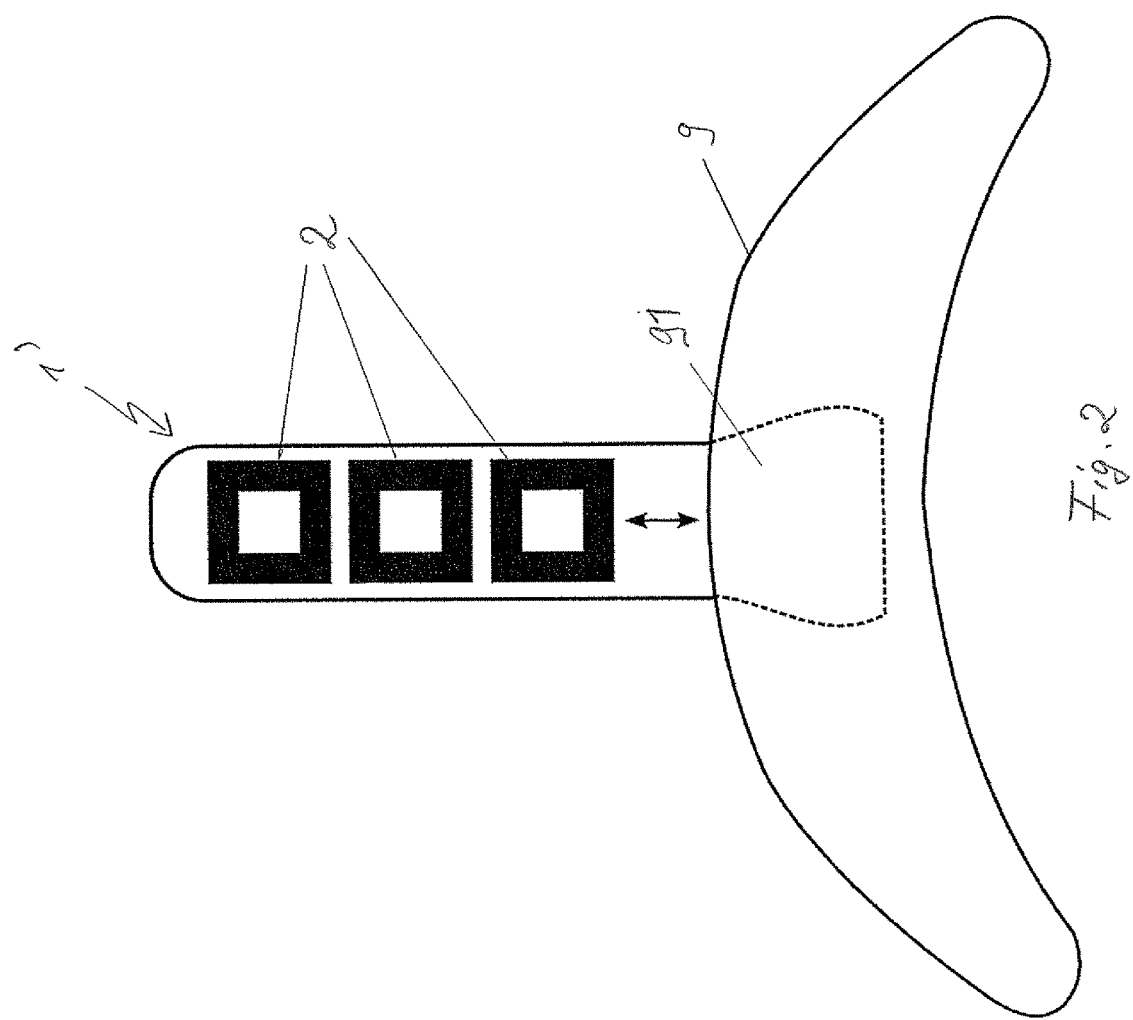
FIG. 2 shows a marker device inserted into the cutting slot of a cutting block.
Figure 3:
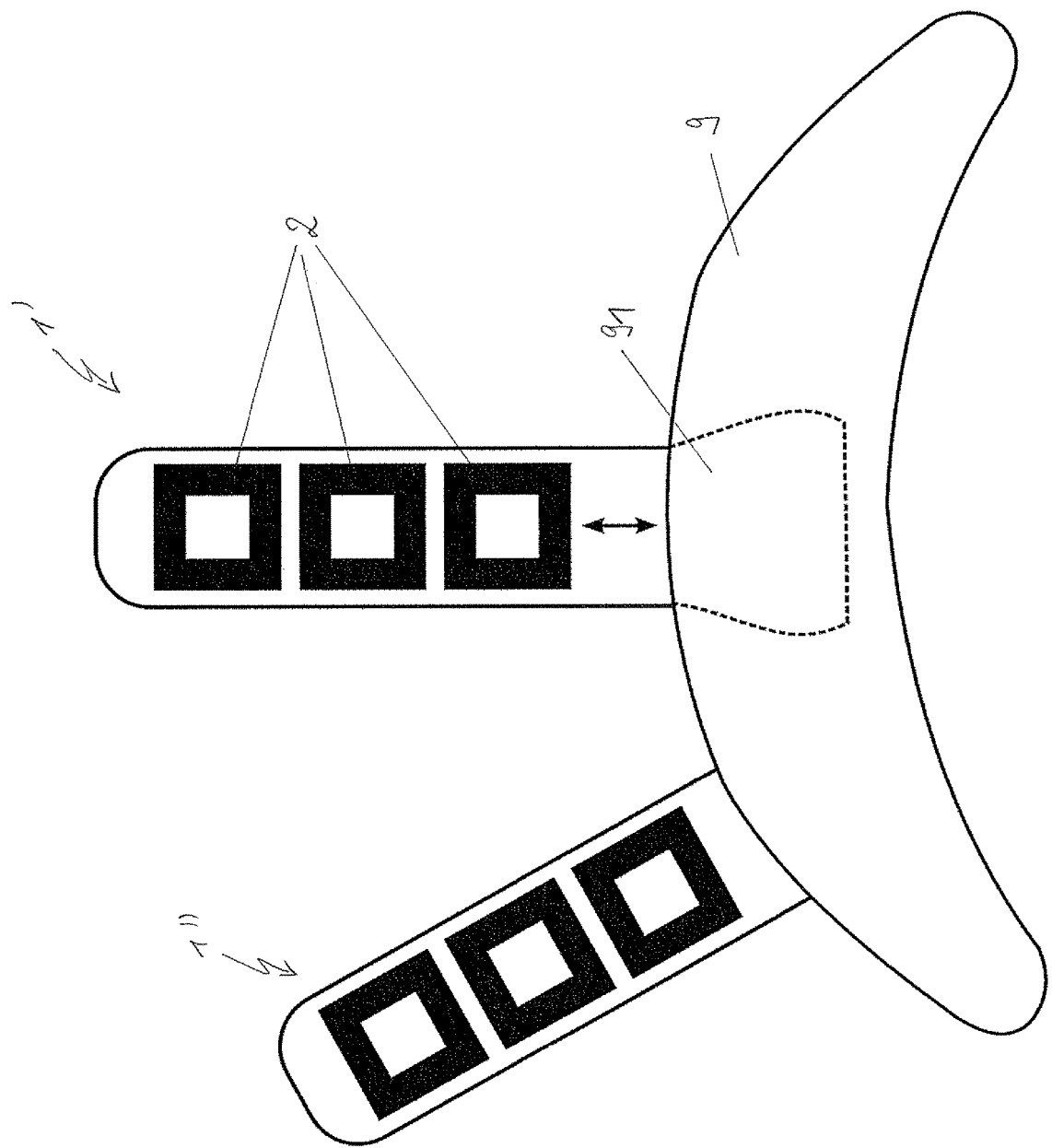
FIG. 3 shows a first marker device inserted into the cutting slot of cutting block and the second marker device relative to which the first marker device can move.
Figure 4:
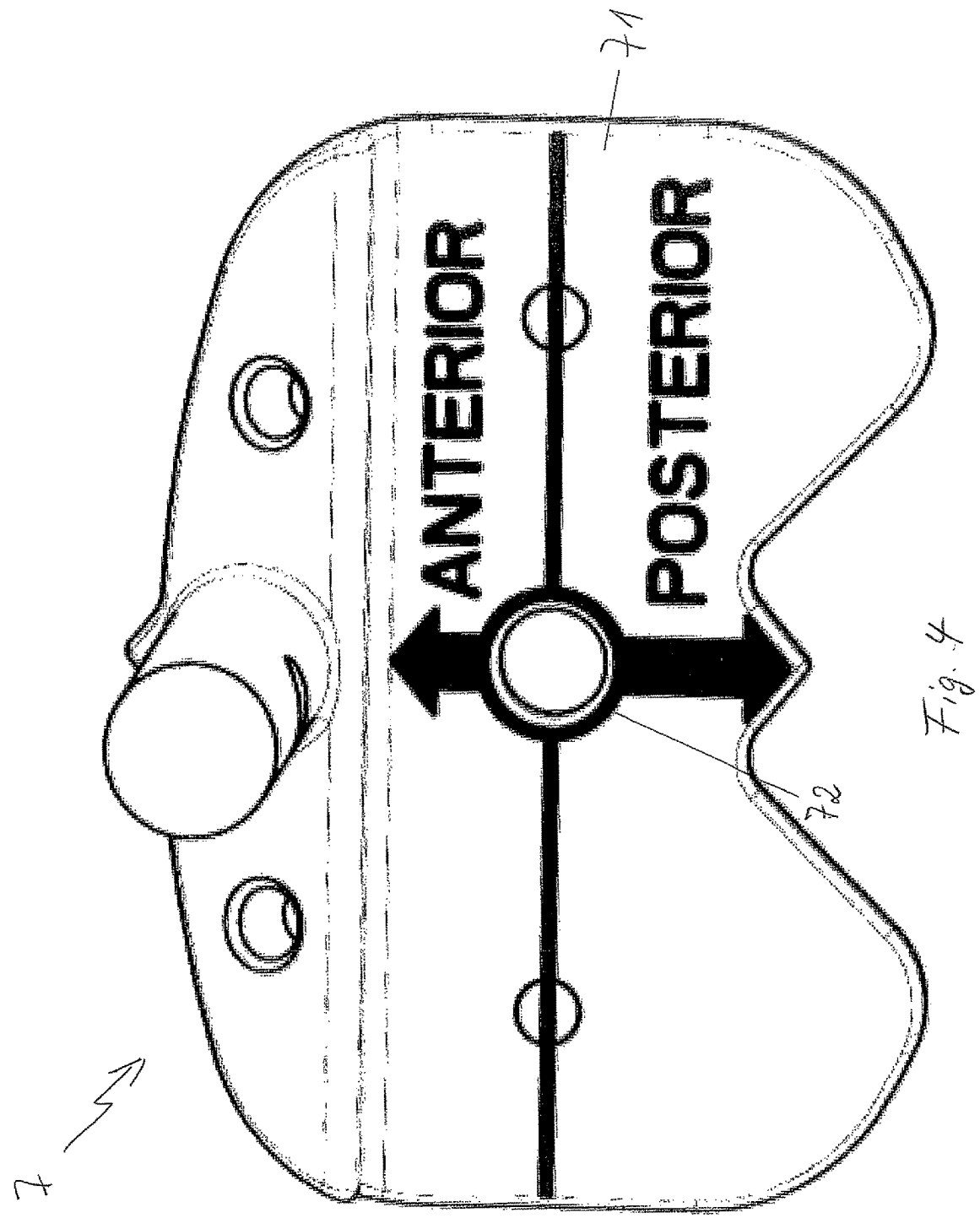
FIG. 4 shows an adapter comprising a planar abutment tool for judging the orientation of a resection plane.
Figure 5:
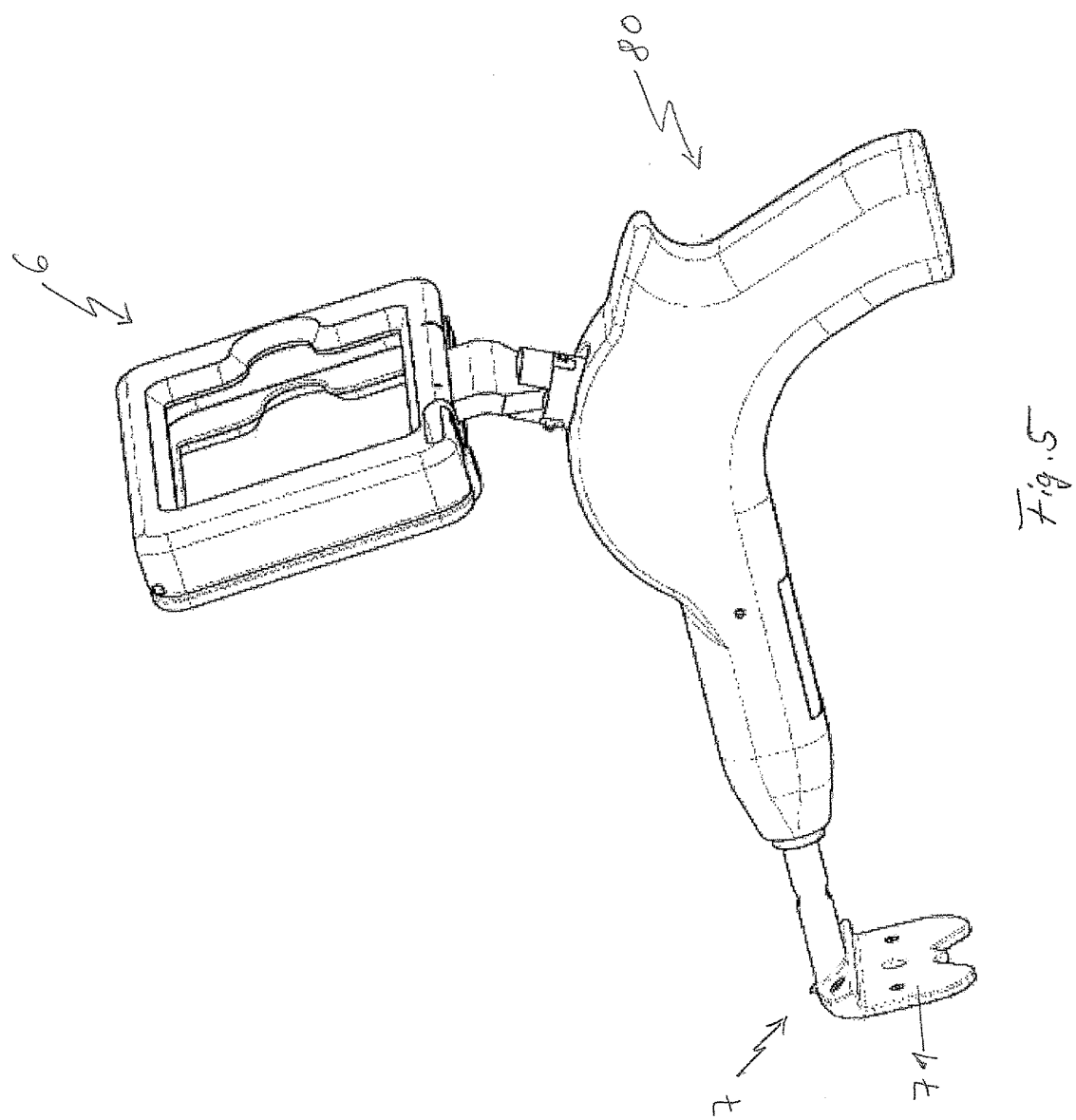
FIG. 5 shows an imaging unit attached to a handle which is provided with the adapter having the planar abutment tool.
Figure 6:
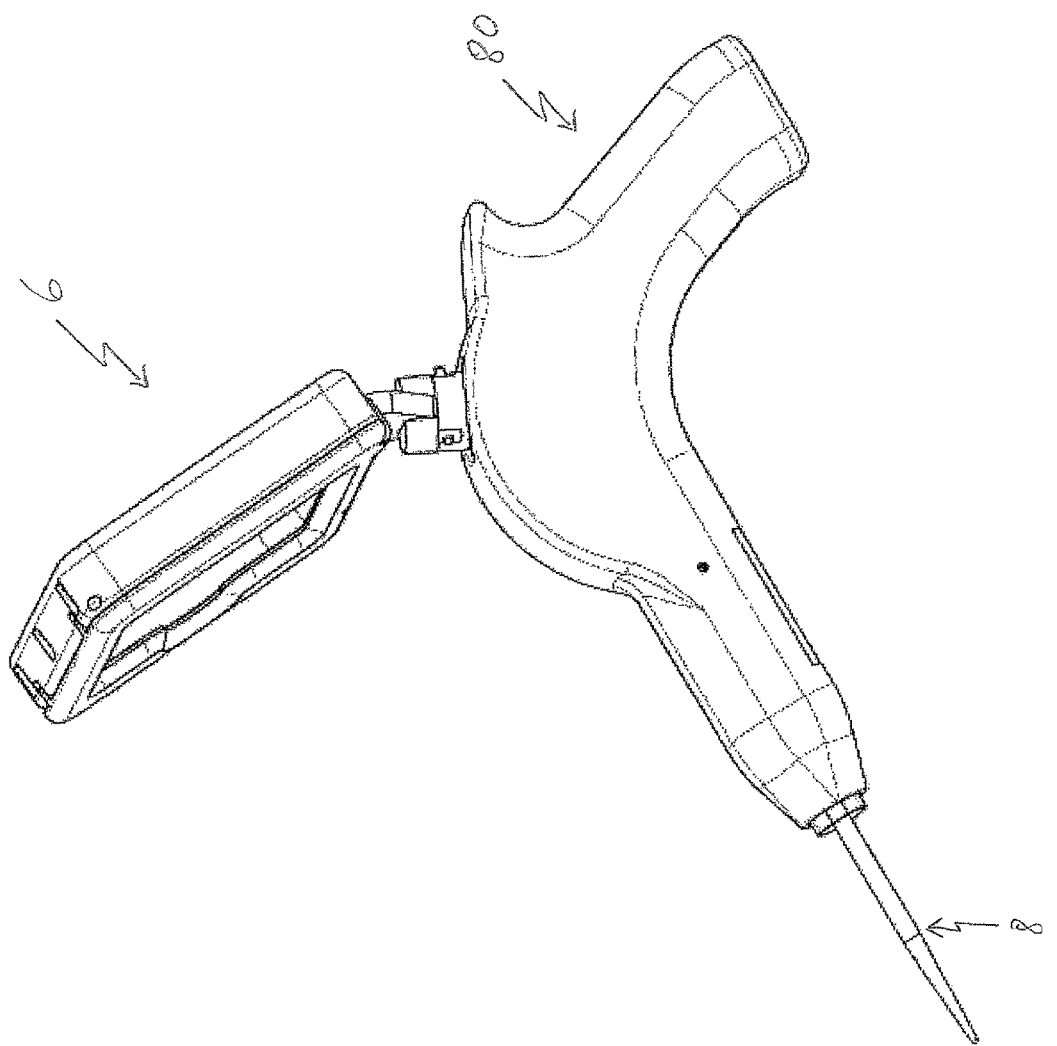
FIG. 6 shows an imaging unit attached to a handle provided with a pointer tool.
Figure 7:
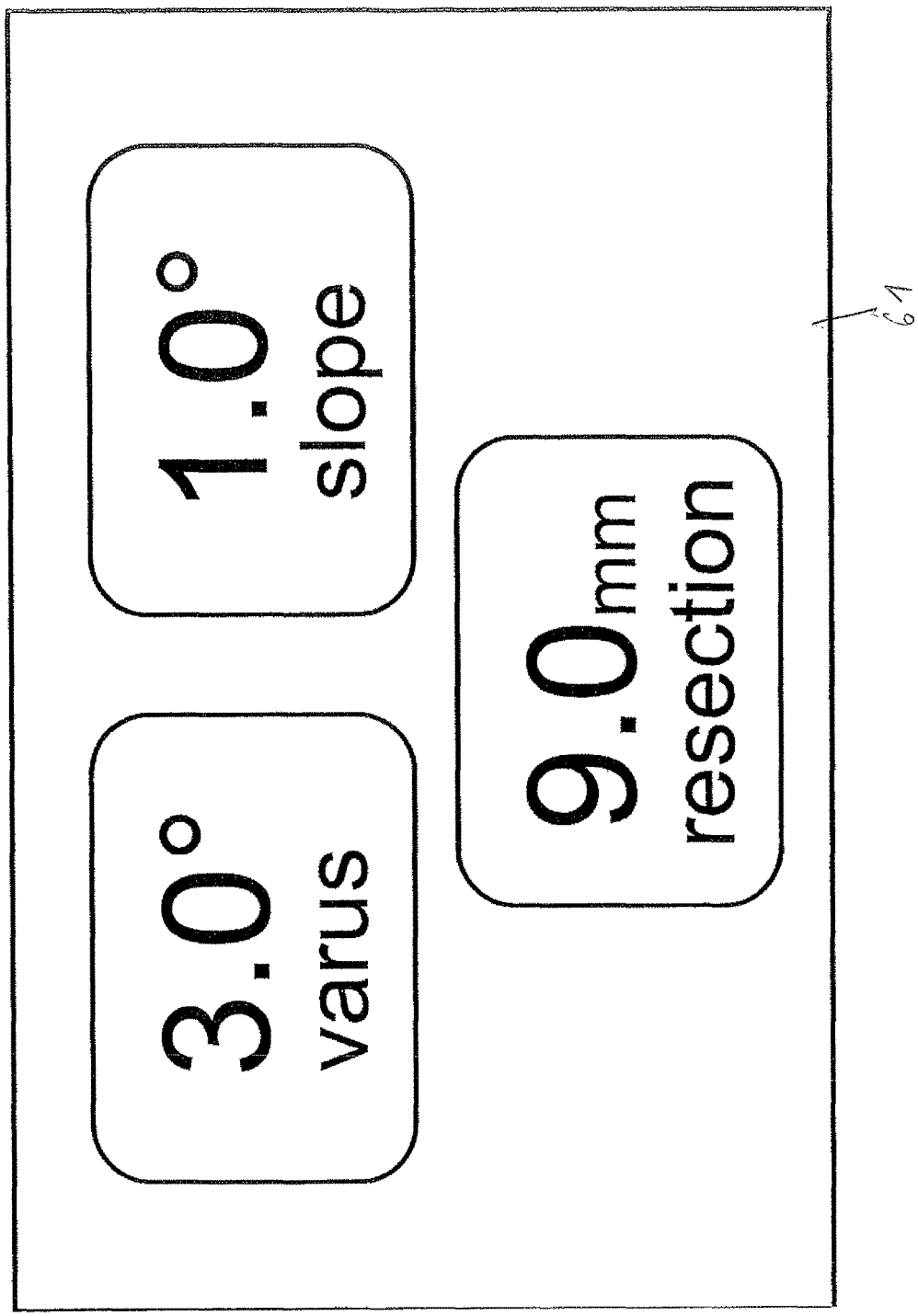
FIG. 7 shows a graphical output of resection plane angular data and resection height data.
Figure 8:
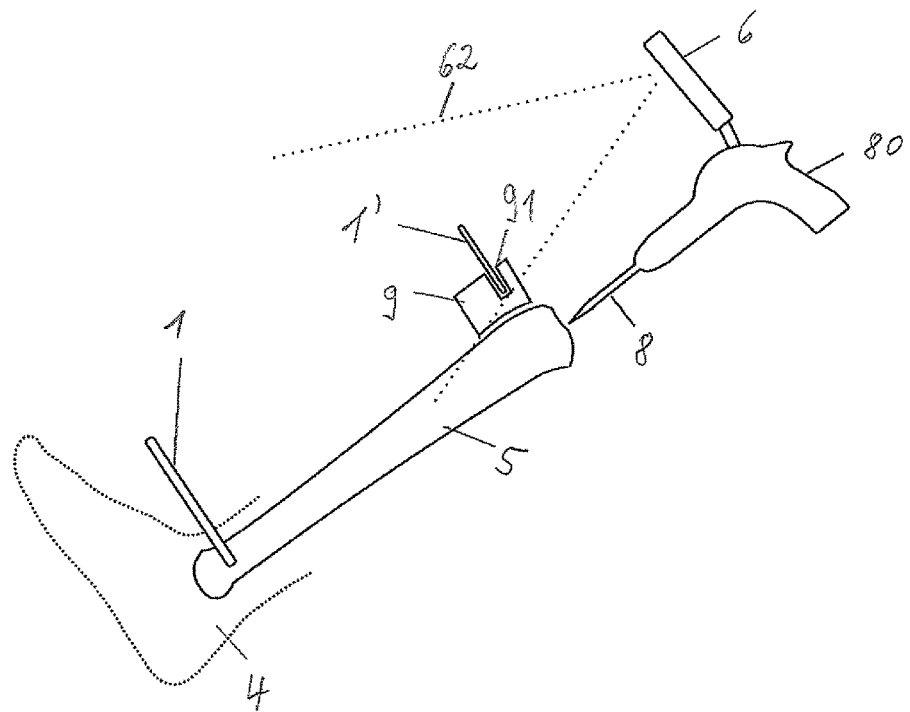
FIG. 8 shows a method for determining the position of a cutting block used for a proximal tibia cut.
Figure 9:
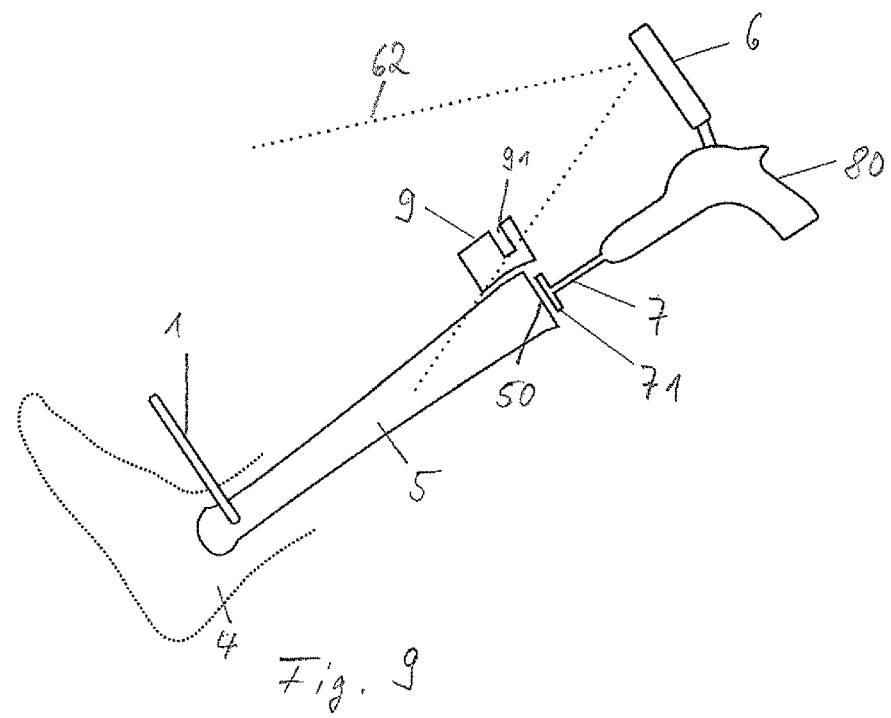
FIG. 9 shows a method for determining the orientation of a finished tibia resection plane.
Figure 11A:
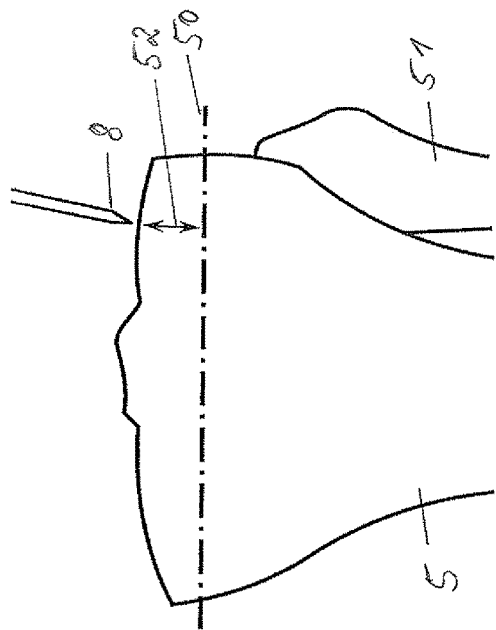
FIG. 11a shows the definition of a tibia resection height.
Figure 11B:
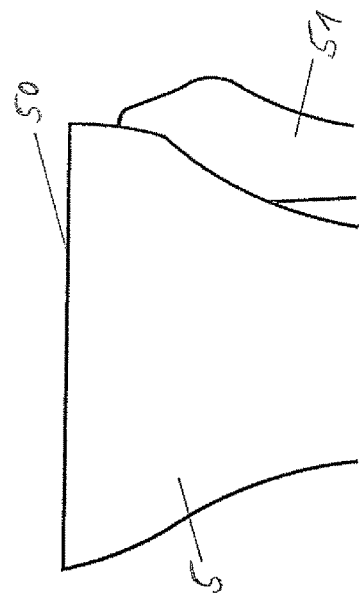
FIG. 11b shows a finished tibia resection plane.
Figure 10A:
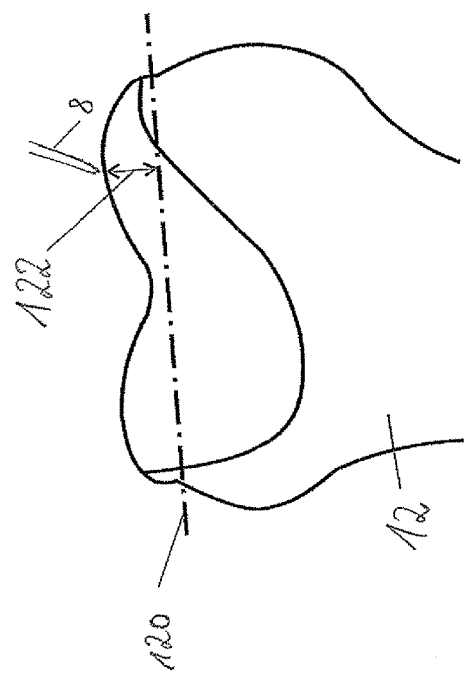
FIG. 10a shows the definition of a femur resection height.
Figure 10B:
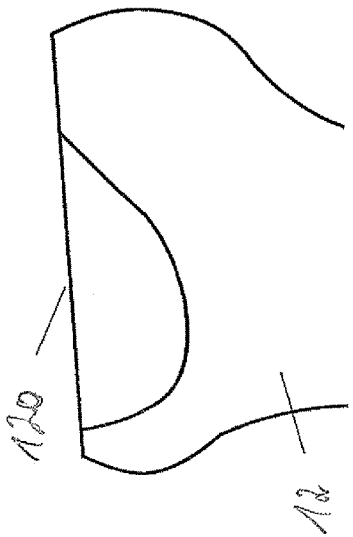
FIG. 10b shows a finished femur resection plane.
Figure 12A:
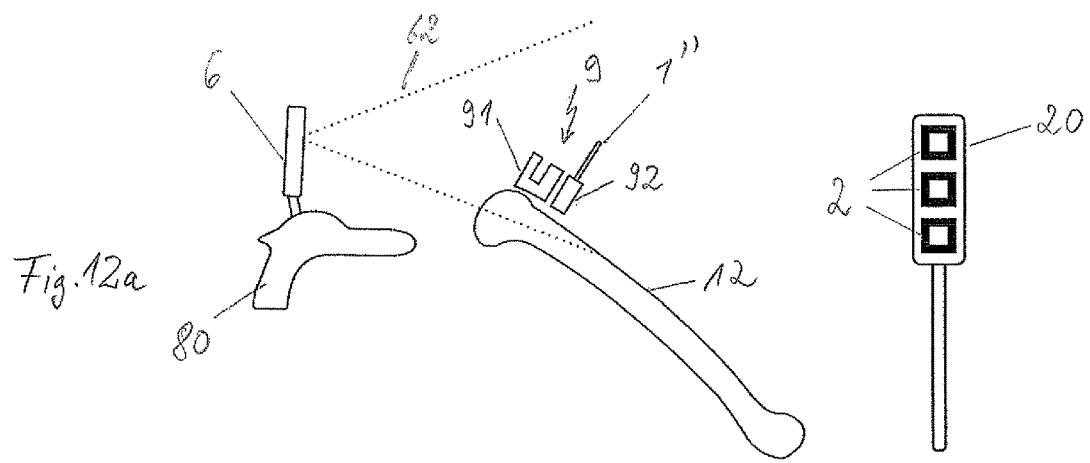
FIGS. 12a to 12c show a first embodiment of a method for planning a distal femur cut and assessing the finished femur resection plane.
Figure 12B:
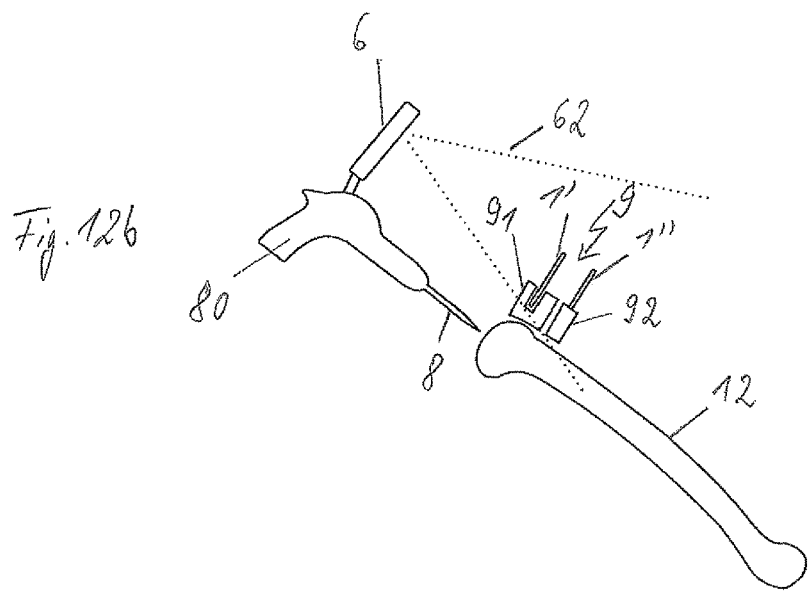
Figure 12C:
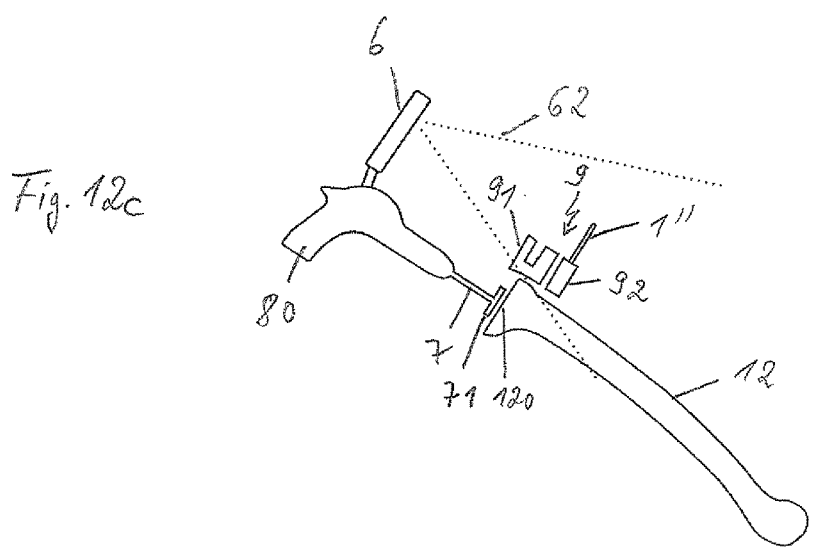
Figure 13A:
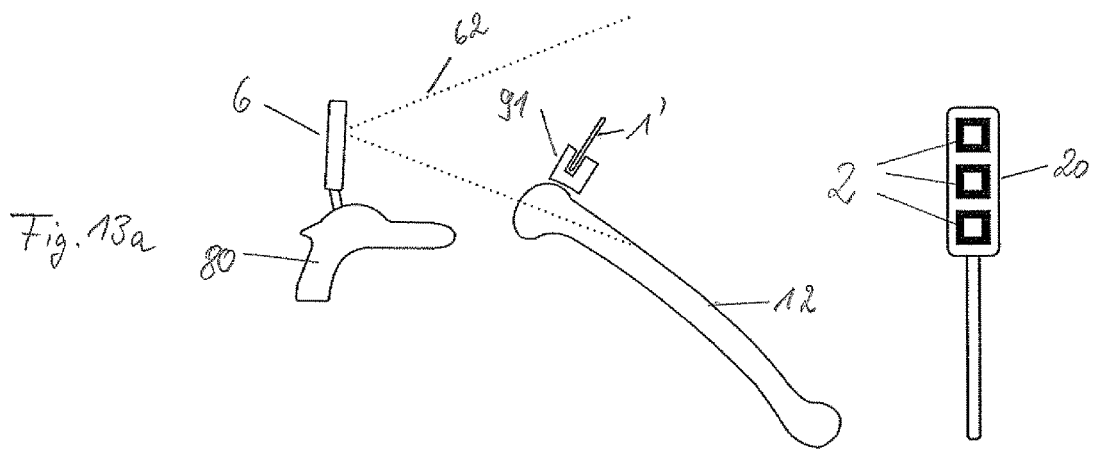
FIGS. 13a to 13c show a second embodiment of the method for planning a distal femur cut and assessing the finished femur resection plane.
Figure 13B:
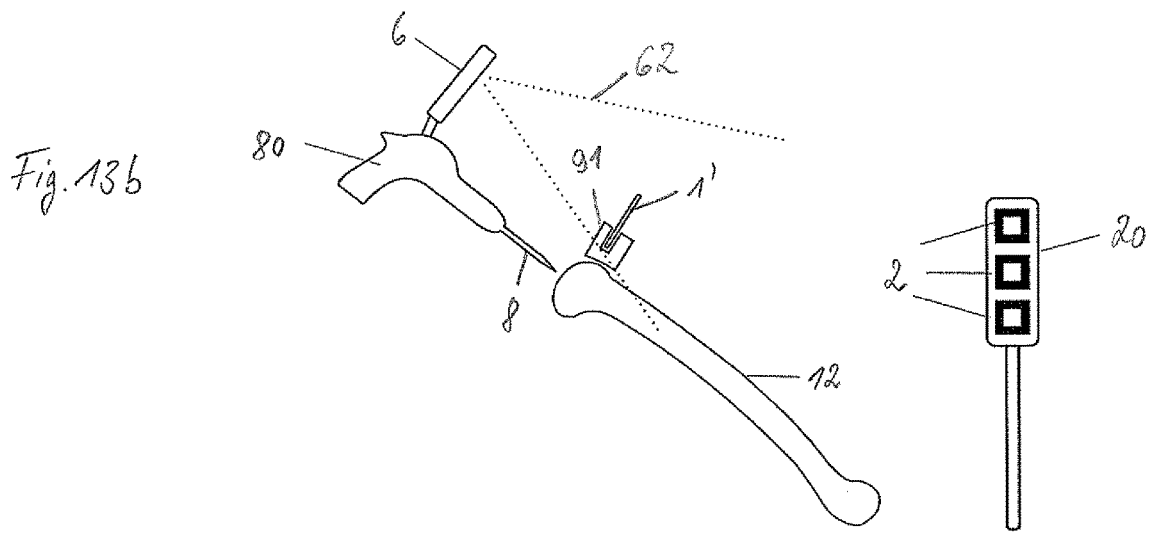
Figure 13C:
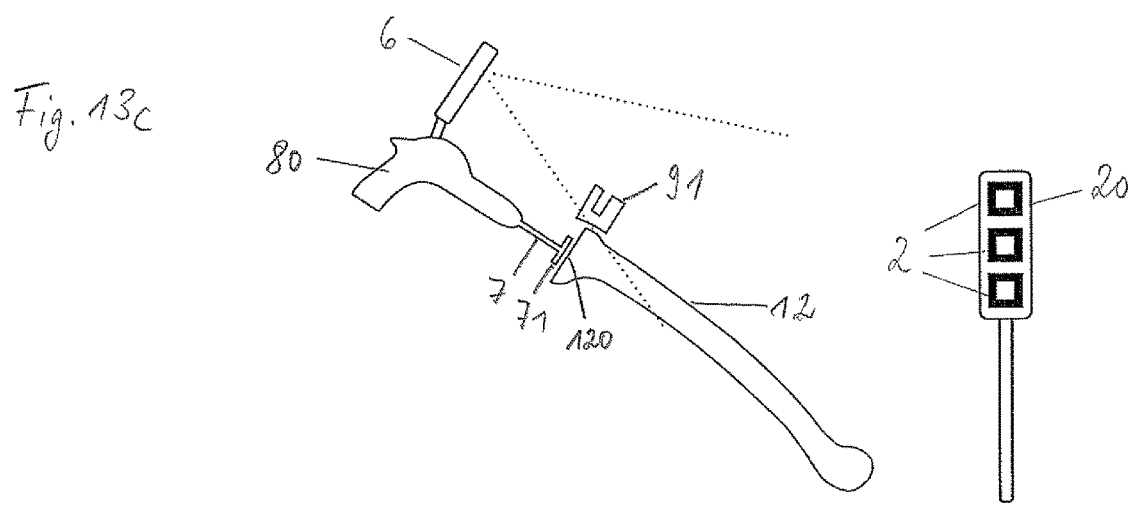
Figure 14A:
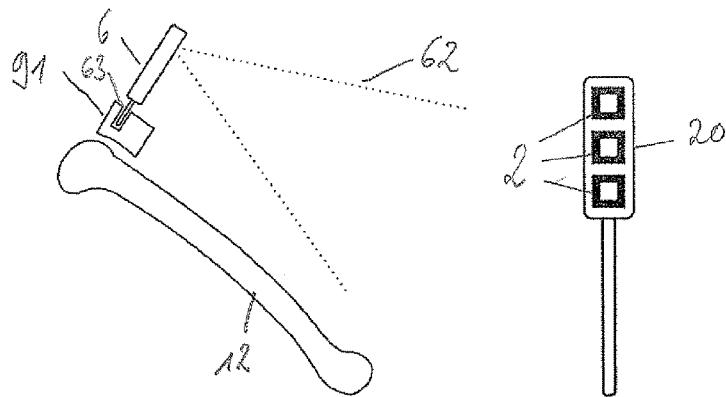
FIGS. 14a to 14c show a third embodiment of the method for planning a distal femur cut and assessing the finished femur resection plane.
Figure 14B:
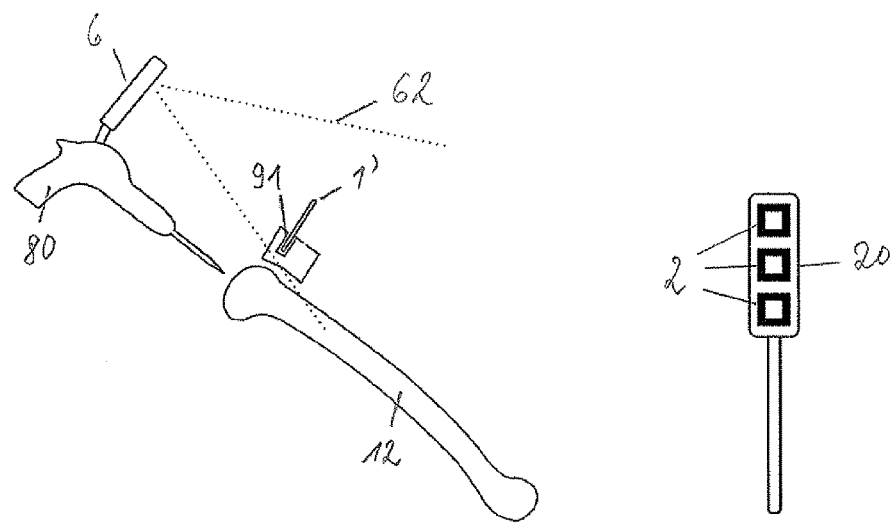
Figure 14C:
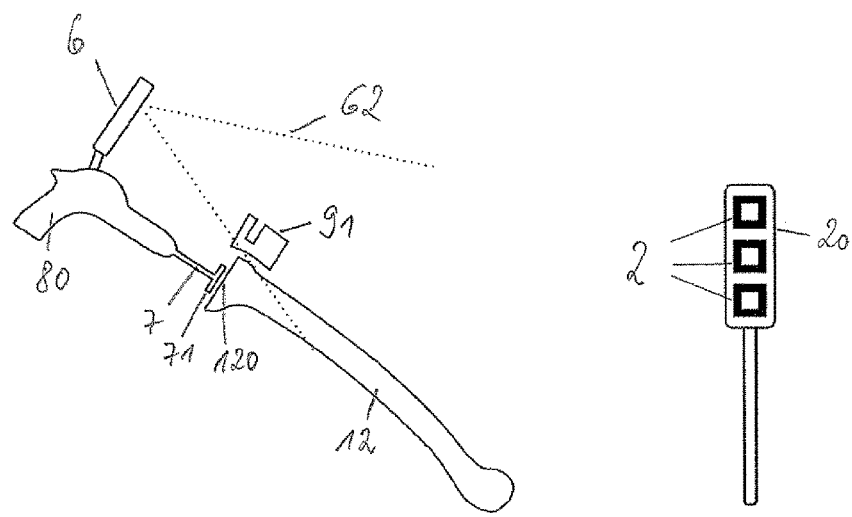
Figure 15:
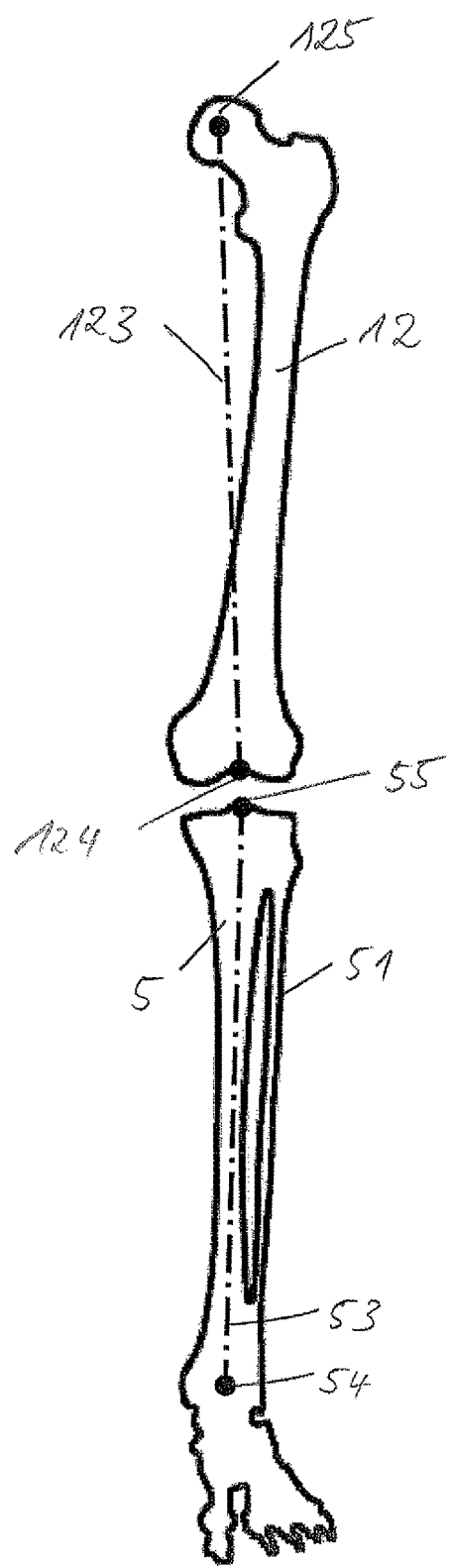
FIG. 15 illustrates the definitions of anatomical features of the femur and the tibia used in the present disclosure.

LIST OF REFERENCE SIGNS 1, 1', 1" marker device
2 graphical patterns/graphical marker patterns
3 attaching mechanism (strap)
4 ankle
5 tibia
6 imaging unit
7 planar adapter
8 pointer adapter
9 cutting block
12 femur
20 (external) marker device
50 tibia resection plane
51 fibula
52 tibia resection height
53 mechanical axis of the tibia (tibia axis)
54 distal end point of the tibia axis
55 proximal end point of the tibia axis
61 display unit
62 viewing area
63 adapter
71 planar abutment piece
72 placement aid
80 handle
91 cutting slot
92 cutting block base
120 femur resection plane
122 femur resection height
123 mechanical axis of the femur (femur axis)
124 distal end point of the femur axis
125 proximal end point of the femur axis

The invention claimed is:

1. A computer-implemented method of determining a spatial relationship between a marker device and a resection plane associated with an anatomical structure of a patient's body, the marker device being video-detectable by an imaging unit, the imaging unit being fastened in a fixed and known spatial relationship to an adapter, the method comprising executing, by a processor of a computer, steps of:
 a) acquiring, at the processor, imaging unit position data describing a predetermined spatial relationship between the imaging unit and the resection plane, the predetermined spatial relationship between the imaging unit and the resection plane being a known spatial relationship between the imaging unit and the resection plane established by a mechanical contact between the adapter and the resection plane;
 b) acquiring, at the processor, marker device position data describing a spatial relationship between the marker device and the imaging unit based on imaging the marker device with the imaging unit in order to generate an orientation-dependent image appearance of the marker device;
 c) determining, by the processor and based on the imaging unit position data acquired in step a) and the marker device position data acquired in step b) and based on the orientation-dependent image appearance of the marker device, resection plane data describing the spatial relationship between the resection plane and the marker device, the spatial relationship between the resection plane and the marker device being defined as the orientation of the resection plane relative to the marker device.

2. The method according to claim 1,
 wherein the predetermined spatial relationship is at least one of position and orientation of the imaging unit relative to the resection plane,
 wherein the spatial relationship between the marker device and the imaging unit is at least one of the position and orientation of the marker device relative to the imaging unit, and
 wherein the spatial relationship between the resection plane and the marker device is at least one of the position and orientation of the resection plane relative to the marker device.

3. The method according to claim 1, further comprising a step of determining, based on the resection plane data, resection height data describing a resection height associated with the position of the resection plane.

4. The method according to claim 1, wherein the imaging unit is a video camera which is combined with a display unit in a single device, which is disposed in a single housing also comprising a display unit.

5. The method according to claim 1, wherein the marker device is a planar marker device comprising a plurality of graphical markers.

6. The method according to claim 1, wherein the marker device has a fixed spatial relationship relative to the resection plane or wherein the marker device does not have a fixed spatial relationship relative to the resection plane.

7. The method according to claim 1, wherein the resection plane data is determined as soon as the marker device is in the viewing area of the imaging unit.

8. The method according to claim 1, wherein the anatomical structure is a tibia and wherein resection plane angular data is determined, by the processor, which describes at least one of a varus/valgus angle and a flexion angle of the resection plane, wherein the resection plane angular data is determined, by the processor, based on the resection plane data, and based on the following:
 data describing the position of the proximal end point of the proximodistal tibia axis;
 data describing the position of the distal end point of the proximodistal tibia axis;
 data describing the orientation of the anteroposterior axis of the distal end of the tibia on the body side with which the resection plane is associated.

9. The method according to claim 8, wherein the data describing the position of the proximal end point of the mechanical, at least one of proximodistal and longitudinal, axis of the tibia is acquired, at the processor, by identifying the position of the proximal end point of the mechanical, at least one of proximodistal and longitudinal, axis of the tibia with a pointer tool having a predetermined, fixed, spatial relationship relative to the imaging unit while imaging the marker device with the imaging unit.

10. The method according to claim 1, wherein the anatomical structure is a femur and wherein resection plane angular data is determined, by the processor, which describes at least one of a varus/valgus angle and a flexion angle of the resection plane, wherein the resection plane angular data is determined, by the processor based on the resection plane position data, and based on the following:

data describing the position of the centre of rotation of the femoral head on the body side with which the resection plane is associated;

data describing the position of the distal end point of the proximodistal femur axis;

data describing the orientation of the anteroposterior axis of the femur on the body side with which the resection plane is associated.

11. The method according to claim 10, wherein the data describing the position of the distal end point of the mechanical, at least one of proximodistal and longitudinal, femur axis is acquired, at the processor, by identifying the position of the distal end point of the mechanical, at least one of proximodistal and longitudinal, femur axis with a pointer tool having a predetermined, fixed, spatial relationship relative to the image unit while imaging the marker device with the imaging unit.

12. The method according to claim 1, wherein the predetermined spatial relationship is defined such that the marker device is in the viewing area of the imaging unit.

13. The method according to claim 1, wherein the predetermined spatial relationship according to step a) has been established by performing one of the following:

placing a planar surface of the adapter flush on a resected portion of the anatomical structure of a patient's body; or inserting the adapter into a cutting block which is attached to the anatomical structure and defines the resection plane.

14. The method according to claim 1, wherein the marker device has been placed on an ankle of the patient on the body side with which the resection plane is associated.

15. The method according to claim 1, wherein the marker device has been placed in a fixed position which is not located on the patient's body.

16. The method according to claim 8, wherein the resection plane angular data is determined based on the orientation of the resection plane relative to the marker device.

17. The method according to claim 10, wherein the resection plane angular data is determined based on the orientation of the resection plane relative to the marker device.

18. A system for determining a spatial relationship between a medical marker device and a resection plane associated with an anatomical structure of a patient's body, the medical marker device being video-detectable by an imaging unit, the system comprising:

an adapter;

the imaging unit for imaging the medical marker device fastened in a fixed and known spatial relationship to the adapter;

a display unit for displaying an image of the marker device; and a computer configured to execute a program which, when executed by the computer, causes a processor of the computer to perform a computer-implemented method of determining a spatial relationship between a marker device and a resection plane associated with an anatomical structure of a patient's body, the marker device being video-detectable by an imaging unit, the method comprising executing, by the processor of the computer, steps of:

a) acquiring, at the processor, imaging unit position data describing a predetermined spatial relationship between the imaging unit and the resection plane, the predetermined spatial relationship between the imaging unit and the resection plane being a known spatial relationship between the imaging unit and the resection plane established by a mechanical contact between the adapter and the resection plane;

b) acquiring, at the processor, marker device position data describing a spatial relationship between the marker device and the imaging unit based on imaging the marker device with the imaging unit in order to generate an orientation-dependent image appearance of the marker device;

c) determining, by the processor and based on the imaging unit position data acquired in step a) and the marker device position data acquired in step b) and based on the orientation-dependent image appearance of the marker device, resection plane data describing the spatial relationship between the resection plane and the marker device, the spatial relationship between the resection plane and the marker device being defined as the orientation of the resection plane relative to the marker device.

19. A non-transitory computer-readable program storage medium storing a program which, when executed on a computer, causes a processor of the computer to execute a computer-implemented method of determining a spatial relationship between a marker device and a resection plane associated with an anatomical structure of a patient's body, the marker device being video-detectable by an imaging unit, the imaging unit being fastened in a fixed and known spatial relationship to an adapter, the method comprising executing, by the processor of the computer, steps of:

a) acquiring, at the processor, imaging unit position data describing a predetermined spatial relationship between the imaging unit and the resection plane, the predetermined spatial relationship between the imaging unit and the resection plane being a known spatial relationship between the imaging unit and the resection plane established by a mechanical contact between the adapter and the resection plane;

b) acquiring, at the processor, marker device position data describing a spatial relationship between the marker device and the imaging unit based on imaging the marker device with the imaging unit in order to generate an orientation-dependent image appearance of the marker device;

c) determining, by the processor and based on the imaging unit position data acquired in step a) and the marker device position data acquired in step b) and based on the orientation-dependent image appearance of the marker device, resection plane data describing the spatial relationship between the resection plane and the marker device, the spatial relationship between the resection plane and the marker device being defined as the orientation of the resection plane relative to the marker device.

* * * * *